(12) United States Patent
Iwabuchi

(10) Patent No.: US 6,861,268 B2
(45) Date of Patent: Mar. 1, 2005

(54) METHOD FOR INSPECTING SILICON WAFER, METHOD FOR MANUFACTURING SILICON WAFER, METHOD FOR FABRICATING SEMICONDUCTOR DEVICE, AND SILICON WAFER

(75) Inventor: Miho Iwabuchi, Fukushima (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 236 days.

(21) Appl. No.: 10/111,500

(22) PCT Filed: Aug. 21, 2001

(86) PCT No.: PCT/JP01/07152

§ 371 (c)(1),
(2), (4) Date: Apr. 24, 2002

(87) PCT Pub. No.: WO02/19414

PCT Pub. Date: Mar. 7, 2002

(65) Prior Publication Data

US 2002/0155630 A1 Oct. 24, 2002

(30) Foreign Application Priority Data

Aug. 31, 2000 (JP) .................................... 2000-262271

(51) Int. Cl.[7] .............................................. H01L 21/66
(52) U.S. Cl. ....................................................... 438/14
(58) Field of Search ........................... 438/14; 356/237.4

(56) References Cited

U.S. PATENT DOCUMENTS 6,515,742 B1 * 2/2003 Ruprecht ................. 356/237.4
6,673,637 B2 * 1/2004 Wack et al. ................. 438/14

FOREIGN PATENT DOCUMENTS

JP         05-017292         1/1993

* cited by examiner

Primary Examiner—John F. Niebling
Assistant Examiner—André C. Stevenson
(74) Attorney, Agent, or Firm—Rader, Fishman & Grauer PLLC

(57) ABSTRACT

The present invention provides a method for inspecting a silicon wafer making it possible to identify and efficiently detect a new defect affecting a device fabricating process, a method for manufacturing a silicon wafer enabling manufacture of wafers not having the defect, a method for fabricating a semiconductor device using the silicon wafer not having this defect, and the silicon wafer not having the defect. When a silicon wafer is inspected, inspection is made for a defect having the entire defect size of 0.5 µm or more in which microdefects gather in a colony state.

6 Claims, 7 Drawing Sheets

METHOD FOR INSPECTING SILICON WAFER, METHOD FOR MANUFACTURING SILICON WAFER, METHOD FOR FABRICATING SEMICONDUCTOR DEVICE, AND SILICON WAFER

TECHNICAL FIELD

The present invention relates to a method for inspecting a silicon wafer (hereinafter may be simply referred to as a "wafer"), and more specifically to a method for inspecting a silicon wafer for detecting a new defect which has not been identified, a method for manufacturing a silicon wafer having no such defect, a method for fabricating a semiconductor device using the silicon wafer having no such defect above, and the new silicon wafer having no such defect.

BACKGROUND ART

Generally a method for manufacturing a silicon wafer comprises a slicing step of slicing a single crystal ingot to obtain a thin disk-shaped wafer; a chamfering step of chamfering a peripheral edge portion of the wafer obtained through the slicing step to prevent cracking and chipping of the wafer; a lapping step of flattening this wafer; an etching step of removing machining deformation remaining in the so chamfered and lapped wafer; a polishing step of making a mirror surface of the wafer; and a cleaning step of cleaning the polished wafer to remove a polishing agent or dust particles deposited thereon. Only the main steps are listed above, and sometimes other steps such as a heat treatment step may be added, or the step sequence may be changed. The silicon wafer manufactured as described above is finally subjected to a quality check, then is packaged in a container for accommodating wafers therein, and is sent to a device fabricating company (or step).

With the manufacturing steps as described above, recently in association with the tendency that devices have been becoming more and more minute, demands for device performance to be achieved have become increasingly severe, and further the silicon wafer is required to have completeness of the crystal quality and cleanliness of the wafer surface.

To satisfy the demands, it is necessary to evaluate quality of the silicon wafer under stringent conditions, and to improve the processing for manufacturing the silicon wafer and fabricating the device using the silicon wafer therein.

In the silicon wafer, completeness of the crystal quality is largely spoiled by existence of impurities, microdefects, strain fields and so on. On the silicon wafer surface, heavy metals, organic materials, particles and surface roughness also cause problems.

As a defect causing a problem in a device fabricating process, there has been known a COP (Crystal Originated Particle) appearing in the vicinity of a surface layer of the wafer. The COP is generally defined as a defect with the size of 0.1 $\mu$m or less, but it appears on the wafer surface as a pit, that is, a defect with the size on the order of 0.1 to 0.5 $\mu$m which can be observed by processing the wafer with an ammonia-hydrogen peroxide solution (also referred to as a "SC1 solution"). These are defects generated when the crystal is pulled.

A FPD (Flow Pattern Defect) having closely related to an oxide film dielectric breakdown strength is a ripple-like defect appearing when preferential etching is performed with an etching liquid based on hydrofluoric acid and potassium bichromate.

There have been known other defects such as a LSTD (Laser Scattering Tomography Defect) detected by the laser scattering tomography, and these defects are microdefects having similar behavior during growth of the crystal.

Further it is known that such defects as an OSF (Oxidation-induced Staking Fault) largely affect performance of a device.

To evaluate these defects, generally preprocessing is performed to a silicon wafer itself prior to start of the evaluation, and then the defects are directly monitored visually, with an electronic microscope or the like.

DISCLOSURE OF THE INVENTION

It has been considered that there may exist other defects affecting the device fabricating step in addition to those described above. It is generally considered that the defects are of different types from the COP, FPD, LSTD, and OSF, but particular features of the defects have not been clarified.

Therefore it has been difficult to accurately and finely evaluate quality of a silicon wafer and to improve the processes for manufacturing the silicon wafer and fabricating a device.

The present inventor has discovered a new type of defect having the entire defect size of 0.5 $\mu$m or more which is different from the crystal defects of the silicon wafer such as a COP previously known and in which microdefects gather in a colony state. This defect may especially affect a yield in the device fabricating step.

This new type of defect is described in more details below. There is no difference between irregularities in the defect area and those in other area of the silicon surface. For instance, this defect can not be detected with an AFM (Atomic Force Microscope) at all.

An atomic force microscope (AFM) monitors a surface by making use of atomic forces working when atoms at the tip of the probe are approached to a sample and controlling the probe for keeping the atomic forces at a constant level. The resolution of the atomic force microscope (AFM) is 0.1 nm or below.

This new type of defect can be detected by performing appropriate image processing with a laser microscope based on a confocal optical system.

The confocal optical system detects quantities of light having passed through a pinhole by irradiating converged light beams on a fine spot on a sample and re-converging the reflected light to the pinhole fitted to the front of a light receiver.

As shown in FIG. 7, a laser microscope 10 based on this confocal optical system comprises a laser light source 14 such as an argon ion laser, a light detector 24 such as a photodiode, a beam splitter 16, a pinhole 20a and others. This laser microscope 10 is described in detail later.

This new type of defect can also be evaluated by cleaning with a SC1 solution. However, this evaluation method becomes problematically a destructive inspection. Further to achieve an easy observation by cleaning with the SC1 solution, the etching time is desired to be longer, but as etching proceeds, the wafer surface becomes rougher, so that the new defect discovered in the present invention can hardly be differentiated from the COP.

As the newly discovered defect described above gives influence on a yield in the device fabricating step, it has been found that the wafer having a defect evaluated and observed by the evaluation method described above should not be sent to the device fabricating step. The present invention has been completed based on the finding.

It is an object of the present invention to provide a method for inspecting a silicon wafer making it possible to identify and efficiently detect a new type of defect affecting a device fabricating step, a method for manufacturing a silicon wafer not having the defect as described above, a method for fabricating a semiconductor device using the silicon wafer not having the defect as described above, and the silicon wafer not having the defect itself.

To solve the problems described above, a method for inspecting a silicon wafer according to the present invention comprises the step of, when inspecting the silicon wafer, inspecting a defect having the entire defect size of 0.5 μm or more in which microdefects gather in a colony state. In this new type of defect, several tens to several hundreds microdefects each having the size on the order of 0.05 to 0.5 μm gather to form a colony-like defect. Depending on the number of gathering microdefects, even the small defect is detectable as one having the size of at least 0.5 μm. There may be found the large defect having the size on the order of 3 to 10 μm.

The defect can be inspected with a laser microscope based on a confocal optical system or a dark field microscope. There is no difference between irregularities in the defect area and those in other area of the wafer surface; therefore the defect can not be evaluated with an atomic force microscope (AFM). After preprocessing is performed with an ammonia-hydrogen peroxide solution (a SC1 solution) and the defect area is etched, the defect may be evaluated and detected, but in this case the inspection becomes a destructive one. Further this type of defect can hardly be differentiated from the conventional type of defect such as a COP. For evaluation as a non-destructive inspection, it is preferable to perform the inspection with the laser microscope based on the confocal optical system.

It has been found that, in addition to the laser microscope based on the confocal optical system, also a dark field microscope can be used for the evaluation. The dark field microscope is used for observing light scattered by defects or particles when irradiating laser beams on a sample to be monitored in the state where the entire measurement system is placed under a dark condition, and also this dark field microscope can be used for the evaluation as a non-destructive inspection.

A first aspect of a method for manufacturing a silicon wafer according to the present invention comprises the steps of: polishing the silicon wafer; cleaning and drying the polished silicon wafer; and inspecting a defect having the entire defect size of 0.5 μm or more in which microdefects gather in a colony state with a laser microscope based on a confocal optical system or a dark field microscope after the cleaning and drying step.

A second aspect of a method for manufacturing a silicon wafer according to the present invention comprises the steps of: mirror polishing the silicon wafer; cleaning and drying the mirror polished silicon wafer; and preventing deposition of impurities on a surface of the wafer and also generation of a defect having the entire defect size of 0.5 μm or more in which microdefects gather in a colony state after the wafer is mirror polished.

A method for fabricating a semiconductor device according to the present invention comprises the steps of: inspecting a defect having the entire defect size of 0.5 μm or more in which microdefects gather in a colony state in a silicon wafer; selecting the silicon wafer not having the defect; and fabricating the semiconductor device by using the silicon wafer not having the defect.

A silicon wafer according to the present invention is the silicon wafer which is mirror polished and has no defect having the entire defect size of 0.5 μm or more in which microdefects gather in a colony state.

This new type of defect to be inspected by the inspecting method according to the present invention is different from any crystal defect, and is conceivably generated by contamination by impurities generated in the polishing step and afterward such as metallic impurities, a non-uniform surface state after polishing (such as the state where alkaline components of a polishing agent remain partially on the surface or hydrophilic areas and hydrophobic areas have been generated), or deposition of silicon particles or other particles floating in the air. Generation of this type of defect can be prevented by preventing deposition of impurities on the wafer surface after polishing.

Therefore, to manufacture a wafer not having the defect as described above, it is required to prevent deposition of impurities immediately after the wafer is polished. For instance, storage of a just polished wafer is conducted in water and the storage water is controlled to manufacture the wafer by adding citric acid and a surfactant, a hydrogen peroxide solution and citric acid, or the like for preventing metals as a kind of the impurities from being deposited on a surface of the wafer. While a final wafer is manufactured, after the storage described above, through several steps including a cleaning step and a packaging step (and an inspecting step), contamination may occur by impurities from the atmosphere during the cleaning and packaging steps after the polishing step, or from, for instance, a container for shipment used for shipping the wafer product, so in the wafer manufacturing process careful attentions are required for preventing the contamination as described above.

By paying careful attentions for preventing contamination by impurities after the polishing step, a wafer not having these defects can be constantly manufactured.

Apart from the above-described wafer manufacturing method, it is also desirable to include a step for inspecting a defect having the entire defect size of 0.5 μm or more in which microdefects gather in a colony state with a laser microscope based on a confocal optical system or a dark field microscope in the manufacturing process and especially to include the inspecting step after the polishing step but before the packaging step.

When the inspecting step is included in the manufacturing process, a wafer which may lower a yield can preferably be removed. Further the laser microscope based on the confocal optical system or the dark field microscope enables a non-destructive inspection, so that the inspecting step can be performed as a part of the general manufacturing process.

By selecting a wafer not having the defect having the entire defect size of 0.5 μm or more as described above in which microdefects gather in a colony state, it is possible to fabricate a device by using the wafer in the device manufacture process with a high yield.

BEST MODE FOR CARRYING OUT THE INVENTION

A laser microscope based on a confocal optical system and a dark field microscope used in the method according to the present invention and procedures for inspecting a wafer with the microscopes are described with reference to FIG. 7, FIG. 8, and FIG. 9, but it is to be noted that the present invention is not limited to the embodiments shown in these figures, and it is needless to say that various modifications are possible within the scope of the technical idea of the present invention.

Figure 7:
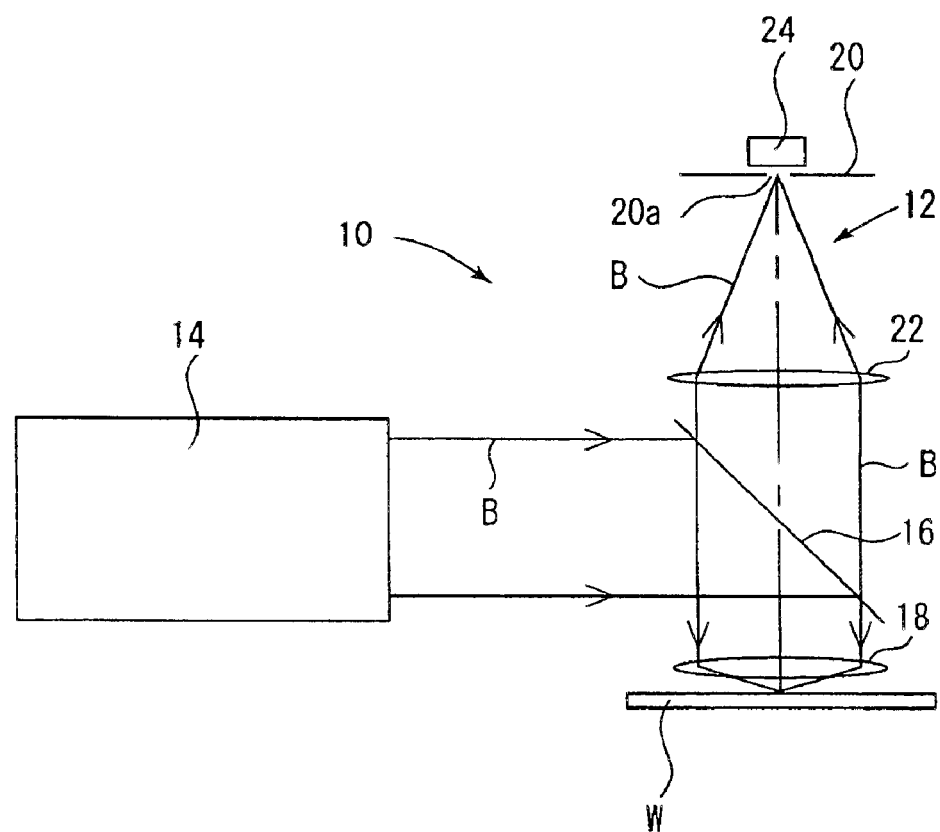
FIG. 7 is a general explanatory view showing a basic structure of the laser microscope based on the confocal optical system.
Figure 8:
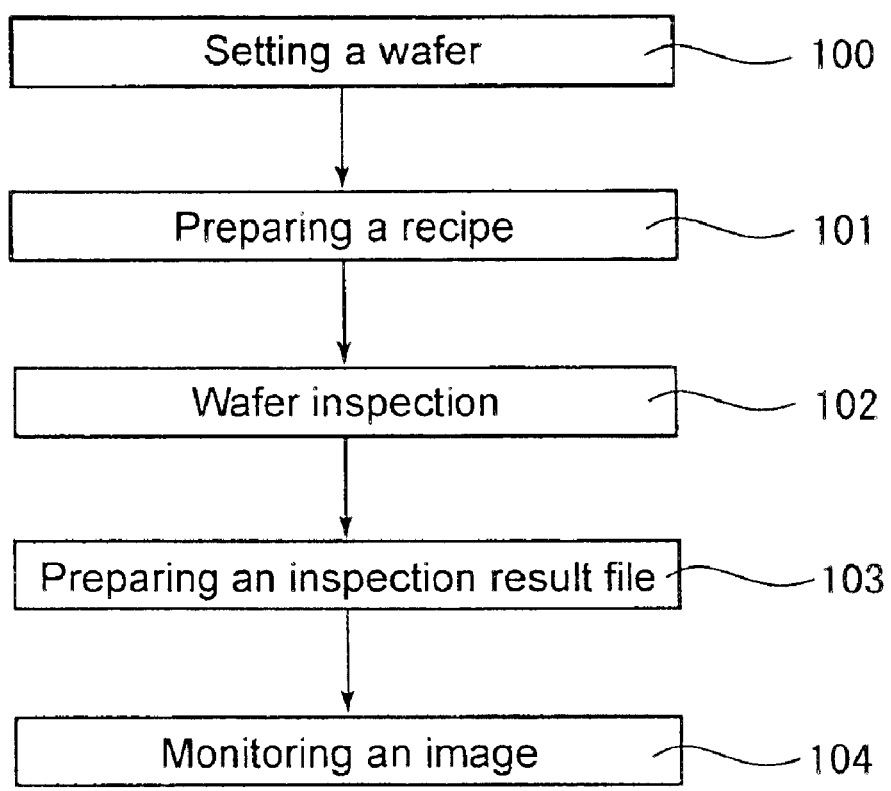
FIG. 8 is a flow chart showing one embodiment of procedures for inspecting the wafer.

FIG. 7 is a general explanatory view showing a basic structure of a laser microscope based on a confocal optical system. In FIG. 7, the reference numeral 10 indicates a laser microscope based on a confocal optical system, in which a laser beam source 14 such as an argon laser is provided at a position opposite to a microscope body 12.

The microscope body 12 comprises a beam splitter 16 for splitting laser beams B from the laser beam source 14 to a plurality of laser beams B, an object lens 18 for converging the laser beams B onto a surface of a wafer W to be inspected, a converging lens 22 for converging the laser beams B reflected from a surface of the wafer W into a pinhole 20*a* of a pinhole member 20, and a light detector 24 for receiving the laser beams B having passed through the pinhole 20*a*.

With the configuration as described above, now the principle of operations thereof is described below.

1) The laser beams B from the laser beam source 14 are split by the laser beam splitter 16 to a plurality of laser beams B.

2) All of the laser beams B are converged and irradiated by the object lens 18 onto a surface of the wafer W with a spot of, for instance, about 0.4 $\mu$m, and concurrently are scanned in the horizontal direction keeping a space between the laser microscope 10 and the wafer W at a constant value.

3) The laser beams B reflected on a surface of the wafer W return through the optical system, and are converged by the converging lens 22 and introduced through the pinhole 20*a* of the pinhole member 20 into the light detector 24.

4) When there are defects on a surface of the wafer W, a wave front of the reflected light from the defect area is disturbed, and a spot of the laser beams B expand, so that the light detecting signal is deteriorated.

5) A defect detecting circuit not shown in the figure detects a difference between signals in the light detector 24, determines that the area where a signal intensity difference with a signal amplitude higher than a prescribed value is generated is a defect area, and records the size and coordinates of the area.

6) An inspection is carried out by moving the laser beams B at a constant speed, and each beam spot scans the entire surface of the wafer W minutely.

Procedures for inspecting the wafer W with the laser microscope 10 based on the confocal optical system described above are described below with reference to FIG. 8. FIG. 8 is a flow chart showing one embodiment of procedures for inspecting the wafer W.

More specifically, the wafer inspecting procedures in the wafer inspecting method according to the present invention are as described below.

1) A wafer is loaded on a wafer cassette and set in a loader section (step 100).

2) An order of wafers to be inspected and a recipe concerning such factors as sensitivity for inspection are prepared in the operator console section (step 101).

3) The wafers to be inspected are automatically aligned and inspected successively (step 102).

4) A defect map and a histogram reflecting a result of inspection in the inspected area are displayed during the wafer inspection, and an inspection result file is automatically prepared (step 103).

5) An image of any defect area specified from the defect map screen can be monitored after completion of the wafer inspection (step 104).

When an optional video printer is used together with the laser microscope based on the confocal optical system used in Examples described below, it is possible to print out a monitor screen. Further the defect area detected as described above can also be analyzed from different points of view by converting the coordinate file format reflecting a result of inspection to a coordinate file format for other devices such as a scanning electron microscope (SEM) or an atomic force microscope (AFM).

Figure 9:
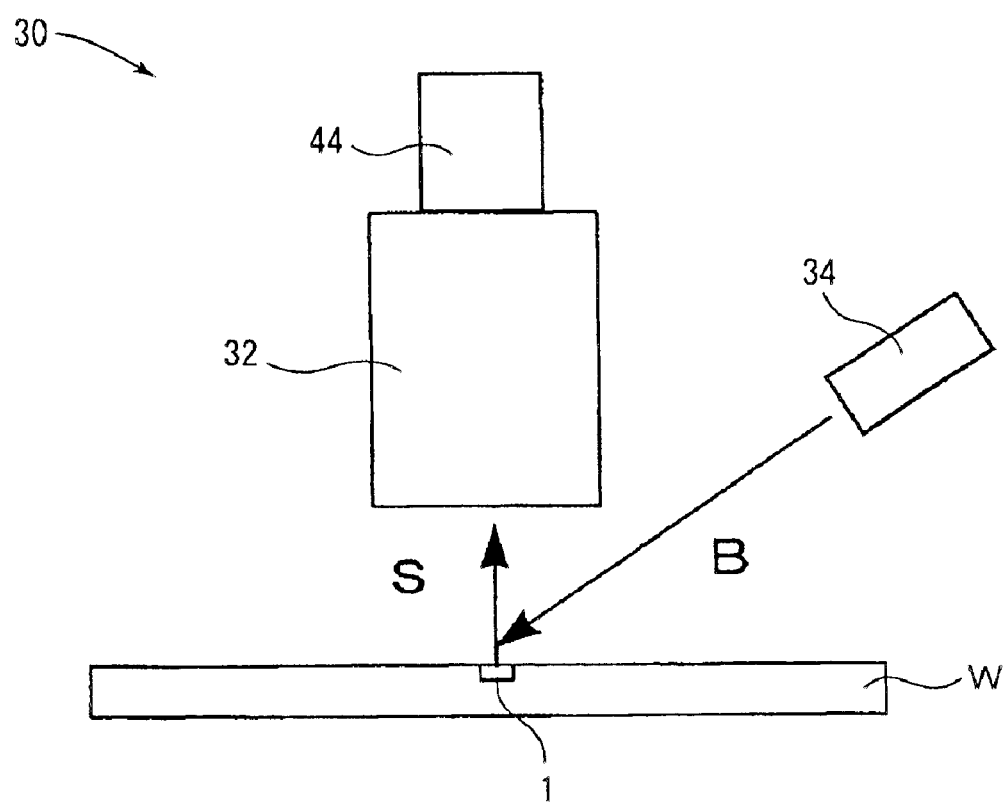
FIG. 9 is a general explanatory view showing a basic structure of a dark field microscope.

FIG. 9 is a general explanatory view showing a basic structure of a dark field microscope. In FIG. 9, the reference numeral 30 indicates a dark field microscope, and the dark field microscope 30 has an optical microscope body 32 with the measurement system set in a dark field. A laser beam source 34 such as an argon laser is provided in relation to the optical microscope body 32. When the laser beams B from the laser beam source 34 are irradiated onto a surface of the wafer W, the laser beams B are scattered due to a defect 1 and the like of the wafer W, and the scattered laser beams S are again converged and detected by a monitoring unit (detector) 44 such as a CCD camera.

With the configuration as described above, now the principle of operations thereof is described below.

1) The laser beams B are irradiated from the laser beam source 34 onto a surface of the wafer W in the state where the measurement system is set in a dark field.

2) When scanning is performed on a surface of the wafer W, the laser beams B are scattered in an area having the defect 1.

3) This scattered light (laser scattering) is converged with an optical microscope and is detected with a detector 44.

EXAMPLES

The present invention will be described more specifically below by way of following Examples which should be construed as illustrative rather than restrictive.

Experimental Example 1

Inspection with a Laser Microscope Based on a Confocal Optical System (Non-destructive Inspection)

A silicon wafer was monitored and inspected with the MAGICS (product name) made by LASERTEC CORP. as a laser microscope based on a confocal optical system. The inspection carried out with the laser microscope based on the confocal optical system is not destructive, and any specific preprocessing is not required.

The sample silicon wafer was manufactured by the general method. Namely, silicon single crystal ingot was sliced, and a peripheral edge portion of the sliced wafer was chamfered to prevent cracking and chipping thereof. The wafer was lapped to be flattened, etched to remove machining deformation, polished for making a mirror surface of the wafer, cleaned and dried. The cleaned and dried sample wafer was evaluated.

Figure 1:
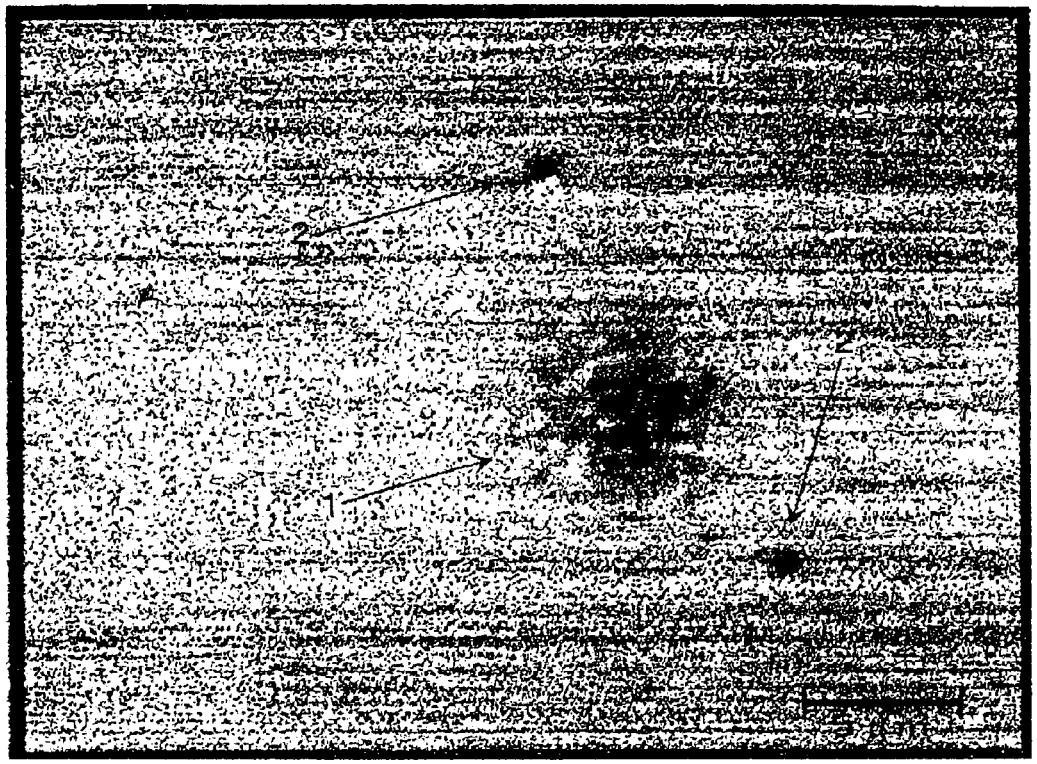
FIG. 1 is a micrograph showing a silicon wafer taken by a laser microscope based on a confocal optical system in Experimental Example 1.
Figure 2:
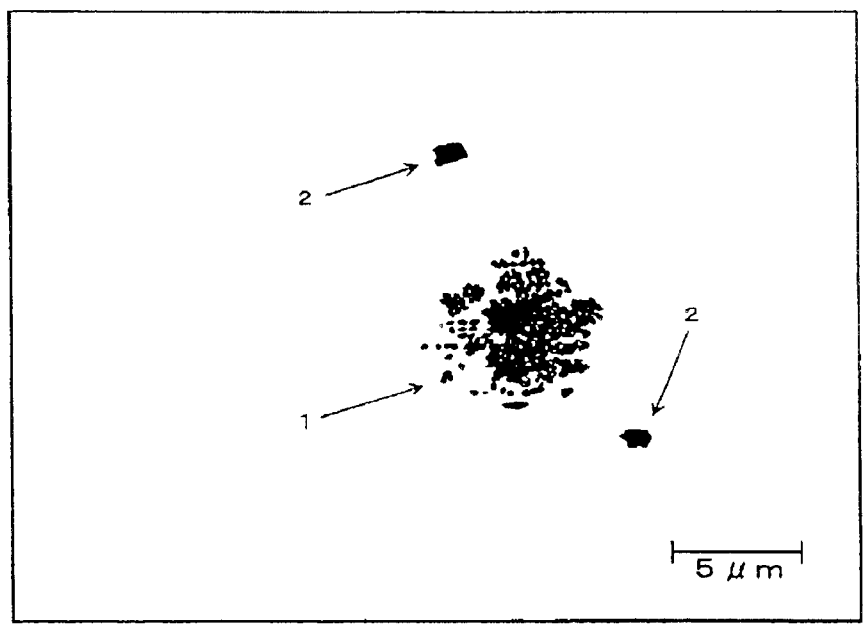
FIG. 2 is a schematic view showing the silicon wafer in FIG. 1.

A result of monitoring the defects is shown in FIG. 1 and FIG. 2. FIG. 1 is a micrograph showing a surface of the sample silicon wafer taken with the MAGICS, and FIG. 2 is a schematic view showing the silicon wafer in FIG. 1. The reference numeral 1 in FIG. 1 and FIG. 2 indicates a defect (defect 1) which may cause troubles in the device fabricating process. From the micrograph of FIG. 1 and the schematic view of FIG. 2, it is understood that dot-like defects gather in the colony state to form a defect area with the size of 0.5 μm or more as a whole. The defect 1 shown in FIG. 1 and FIG. 2 indicates a representative defect observed on a wafer surface. The entire size of each defect varies according to the gathering state of the microdefects, but a plurality of defects 1 each having the similar colony-like form and the size on the order of 0.5 μm to 10 μm were observed on the wafer surface. The size of the defect 1 shown in FIG. 1 and FIG. 2 was about 6 μm.

The reference numeral 2 in FIG. 1 and FIG. 2 indicates a defect (defect 2) which can be observed with an atomic force microscope (AFM). This defect 2 was used as a mark so that the defect 2 could be confirmed at the same position also in other evaluation methods. Namely, monitoring was performed under a fixed point observation.

Then irregularities of the defect surface were evaluated with the atomic force microscope (AFM). The SPA 360 from SEIKO INSTRUMENTS INC. was used as the atomic force microscope (AFM).

Figure 3:
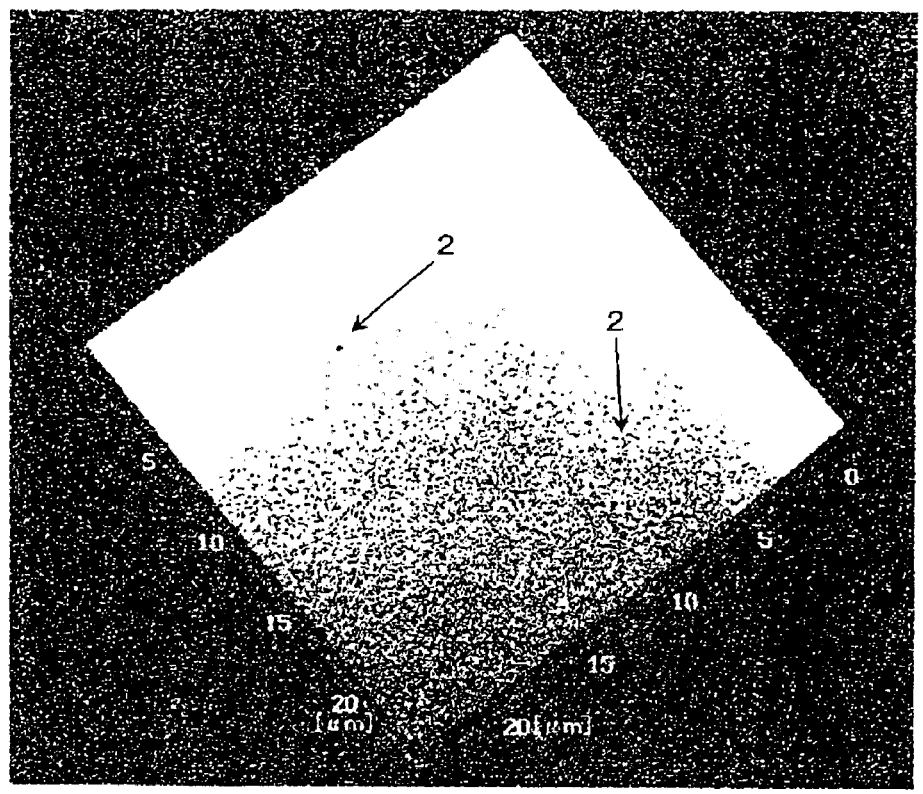
FIG. 3 is a micrograph showing a silicon wafer taken by an atomic force microscope (AFM) in Experimental Example 1.
Figure 4:
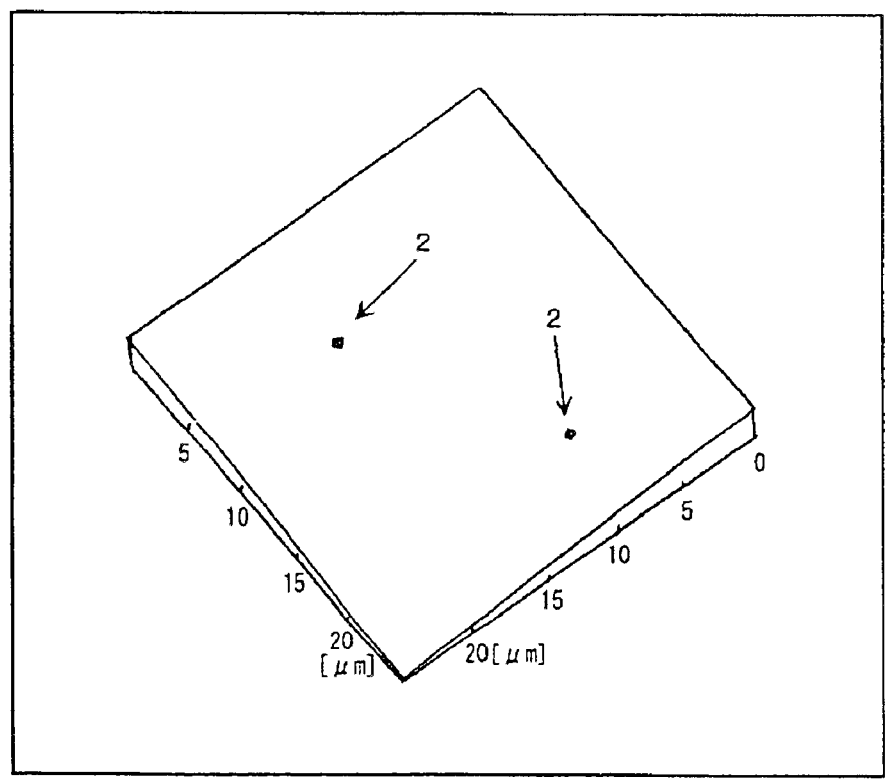
FIG. 4 is a schematic view showing the silicon wafer in FIG. 3.

Using the defect 2 as a mark, the defect was confirmed at the same position in FIG. 1 and FIG. 2. A result of monitoring with the atomic force microscope (AFM) is shown in FIG. 3. FIG. 3 is a micrograph showing a surface of the silicon wafer taken with the SPA 360, while FIG. 4 is a schematic view showing the silicon surface in FIG. 3. As clearly understood from FIG. 3 and FIG. 4, the defect 1 observed in FIG. 1 and FIG. 2 could not be detected even when irregularities of the wafer surface were monitored with the atomic force microscope (AFM), and it is considered that this defect has no irregularities and that this defect is caused by impurities gathering in a strained portion within the wafer (an uppermost surface layer).

Experimental Example 2

Inspection After Long Time Processing with a SC1 Solution (Destructive Inspection)

The silicon wafer observed in Experimental Example 1 was processed with a SC1 solution (a chemical solution with the volumetric ratio of 28 wt % ammonia water: 30 wt % hydrogen peroxide solution: water=10:2:100) for 40 minutes under the solution temperature of 80° C. The wafer immersed in the solution was then monitored and inspected with an atomic force microscope (AFM).

Figure 5:
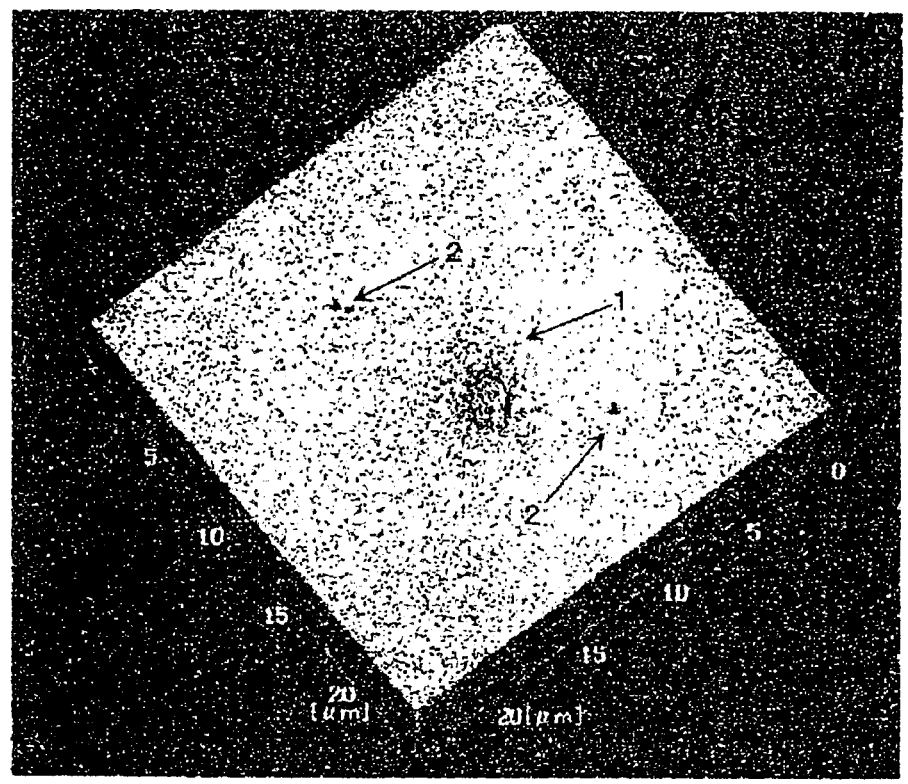
FIG. 5 is a micrograph showing a silicon wafer taken by an atomic force microscope (AFM) in Experimental Example 2.
Figure 6:
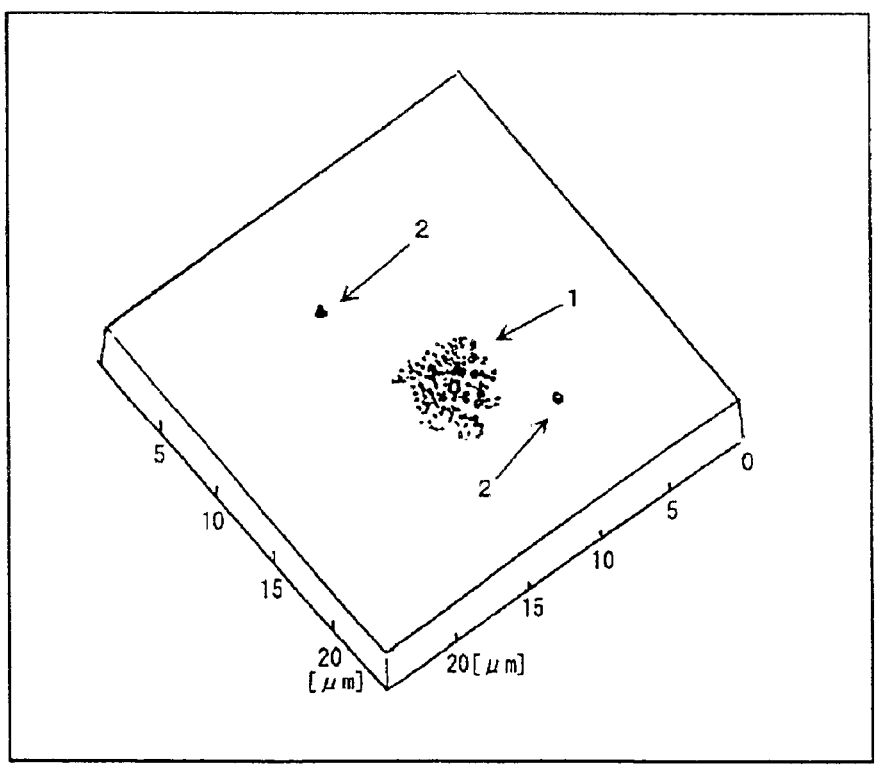
FIG. 6 is a schematic view showing the silicon wafer in FIG. 5.

A result of observation of the defect is shown in FIG. 5 and FIG. 6. FIG. 5 is a micrograph showing a surface of the silicon wafer taken with the SPA 360, while FIG. 6 is a schematic view showing the surface of silicon wafer shown in FIG. 5. The area of defect 1 not observed with the atomic force microscope (AFM) (see FIG. 3 and FIG. 4) was etched with a chemical solution with the SC1 composition, and the defect 1 could be observed as shown in FIG. 5 and FIG. 6.

As described above, this new defect 1 is different from a defect caused due to the crystalline structure such as a COP, and it can be considered that this defect is caused due to any defect in an uppermost surface layer of the wafer surface, especially strain therein.

Experimental Example 3

Inspection with a Dark Field Microscope

A silicon wafer was observed with the SPA 360 from SEIKO INSTRUMENTS INC. as a dark field microscope. This SPA 360 is a unit provided with different two types of microscopes, namely the atomic force microscope (AFM) and the dark field microscope, and this unit enables observation with a dark field microscope at the same position where measurement is performed with the AFM.

The sample silicon wafer was a wafer with a defect having the entire defect size of 0.5 μm or more in which microdefects gather in a colony state (the wafer used in Experimental Example 1), and the defect was confirmed with a laser microscope based on the confocal optical system.

Figure 10:
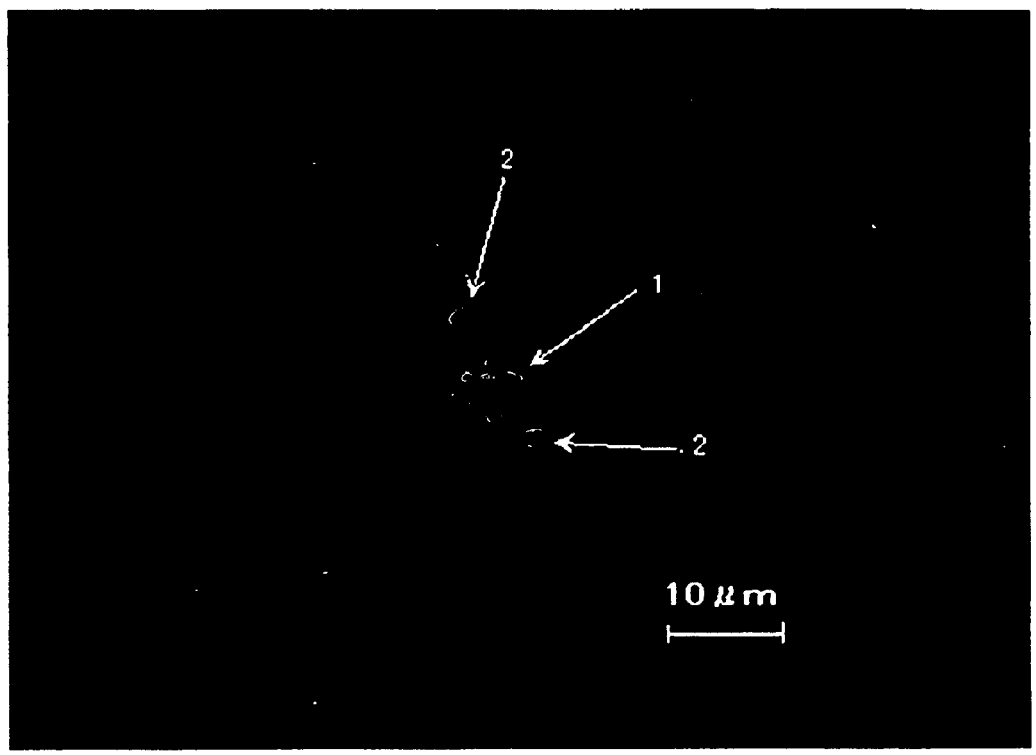
FIG. 10 is a micrograph showing a silicon wafer taken by the dark field microscope in Experimental Example 3.
Figure 11:
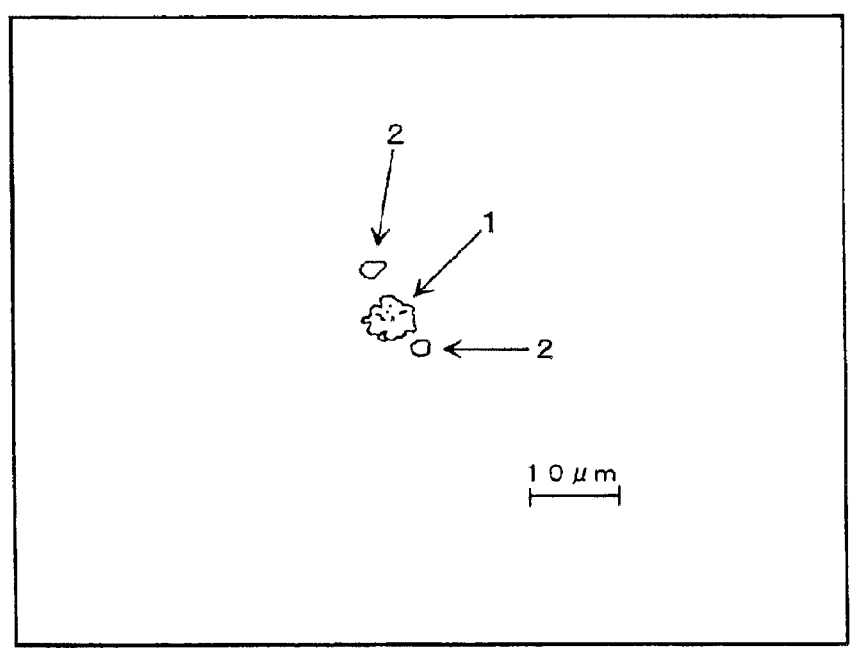
FIG. 11 is a schematic view showing the silicon wafer in FIG. 10.

A result of observation of the defect is shown in FIG. 10 and FIG. 11. FIG. 10 is a micrograph showing the silicon wafer taken with a dark field microscope, while FIG. 11 is a schematic view showing the silicon wafer shown in FIG. 10. Observation was performed at about ×50 magnification. Although the microdefects can not be differentiated from each other, these figures show that the defect having the same form as that of the defect 1 observed with the laser microscope based on the confocal optical system can be observed. A defect having the ordinary irregularities (such as the defect 2 observed as a mark) or a particle can be detected with the dark field microscope because scattering of the laser beams occurs, but it was found that also the defect having no irregularities found in the present invention could be observed with the dark field microscope. It can be considered that this new type of defect can be observed with the dark field microscope because this defect is a specific one. Namely, although this defect has no irregularities, it can be considered that the defect reflects a difference in surface quality between the defect area and other normal area in the vicinity thereof, especially a difference in density due to impurities present on the wafer surface.

Example 1

A sample silicon wafer subjected up to the polishing step by following the same sequence as that in Experimental Example 1 was prepared, and the polished sample wafer was stored in a pit tank containing citric acid and hydrogen peroxide solution to prevent impurities such as metal contamination as much as possible, and then was subjected to the cleaning step. Contamination by heavy metals was prevented also during this cleaning step, and then the sample was dried. Even after the steps described above, the sample was kept under an environment where the quantities of particles in the atmospheric air were 1000 pieces per cubic feet or less, and the sample wafer was monitored and evaluated with a laser microscope based on a confocal optical system immediately after the sample was taken out from the environment. The defect 1 having the entire defect size of 0.5 µm or more in which microdefects gather in a colony state as shown in FIG. 1 was not observed.

Comparative Example 1

A sample silicon wafer subjected up to the polishing step by following the same sequence as that in Experimental Example 1 was prepared, and the polished sample wafer was stored in pure water, took out from the water and left intentionally under the atmospheric air for a while, and then was cleaned. In these steps, the sample wafer was intentionally contacted to unspecified impurities. Then the sample silicon wafer was monitored and evaluated with a laser microscope based on a confocal optical system. A plurality of defects 1 having the entire defect size of 0.5 µm or more in which microdefects gather in a colony state as shown in FIG. 1 and FIG. 2 were observed. In the wafers (8-inch wafer) observed as described above, 10 to 30 colony-like defects each having the size on the order of 1 to 5 µm were present on a surface of the wafer, especially in the peripheral area thereof.

Manufacturing Example 1

The wafer manufacturing process described hereinafter comprises a step for inspecting a defect having the entire defect size of 0.5 µm or more in which microdefects gather in a colony state with a laser microscope based on a confocal optical system, and the inspecting step was located between a cleaning and drying step and a packaging step.

Steps up to the cleaning and drying step in the wafer manufacturing process were carried out in a plurality of lines to evaluate wafers. The above-described defect was observed in some lines, but was not observed in other lines. In the manufacturing process wherein the defect was observed, the water used for storing a polished wafer was only pure water. When hydrogen peroxide solution and citric acid were added to the water for storing wafers therein, the defect was not observed in the wafer manufactured in the line. As described above, the manufacturing process can be improved by the use of the result obtained in the inspection step with the laser microscope based on the confocal optical system.

When the wafer recognized as having a defect, especially a wafer having the relatively larger defect with the size of 0.5 µm or more was used in the device fabricating process, the yield became lower. In the inspecting step, the defect was recognized visually or by the image processing, and wafers not having the defect were selected and used in the device fabricating process, so that the yield was improved.

From the results of various experiments described above, a new defect affecting the yield in the device fabricating process was found. It was also confirmed that the wafer not having the defect as described above showed the excellent performance. Further it was found that the defect could easily be found with a laser microscope based on a confocal optical system. Therefore by selecting only wafers not having the defect and sending the selected wafers to the device fabricating process, the yield can be improved. It was also found that it was required to prevent and control contamination by impurities after polishing for protection against this type of defect. Also it was found that the defect could be detected, in addition to the laser microscope based on the confocal optical system, also with a dark field microscope, and that, in that case, the same effect as that obtained by the laser microscope could be obtained. It is preferable to use a microscope capable of sensing a change in a quantity of detected light (difference in contrast).

It is to be noted that the present invention is not limited to the embodiments described above. For instance, the defect which can be observed with the laser microscope based on the confocal optical system or the like, namely the defect without irregularities having the entire defect size of 0.5 µm or more in which microdefects gather in a colony state is often observed after the polishing step. It can be considered that, as a surface of a polished wafer is in an active state, the surface is easily affected when the surface is contacted to impurities which are considered to be a cause for the defect. The active state of the wafer surface is also generated after epitaxial growth or on a surface of a wafer processed by, for instance, a hydrofluoric acid solution, with the result that similar defects may be observed. Inspection of wafers after epitaxial growth or wafers processed by hydrofluoric acid and selection of wafers having no defect after these steps are also included in a technical scope of the present invention.

Capability of Exploitation in Industry

As described above, with the method for inspecting a silicon wafer according to the present invention, it is possible to efficiently detect and identify a new defect of a silicon wafer which may affect a device fabricating process (a defect having the entire defect size of 0.5 µm or more in which microdefects gather in a colony state). With the method for manufacturing a silicon wafer according to the present invention, a wafer not having this new type of defect can be manufactured. Further with the method for fabricating a device according to the present invention, the yield in the device fabricating process can be improved by using a silicon wafer not having this new type of defect. The silicon wafer according to the present invention does not have this new type of defect, and can contribute to improvement of yield in the device fabricating process.

What is claimed is:

1. A method for inspecting a silicon wafer comprising the step of, when inspecting the silicon wafer, inspecting a defect having the entire defect size of 0.5 µm or more in which microdefects gather in a colony state.

2. A method for inspecting a silicon wafer according to claim 1, wherein the defect is inspected with a laser microscope based on a confocal optical system or a dark field microscope.

3. A method for manufacturing a silicon wafer comprising the steps of:

polishing the silicon wafer;

cleaning and drying the polished silicon wafer; and inspecting a defect having the entire defect size of 0.5 µm or more in which microdefects gather in a colony state with a laser microscope based on a confocal optical system or a dark field microscope after the cleaning and drying step.

4. A method for manufacturing a silicon wafer comprising the steps of:

mirror polishing the silicon wafer;

cleaning and drying the mirror polished silicon wafer; and preventing deposition of impurities on a surface of the wafer and also generation of a defect having the entire defect size of 0.5 μm or more in which microdefects gather in a colony state after the wafer is mirror polished.

5. A method of fabricating a semiconductor device comprising the steps of:

inspecting a defect having the entire defect size of 0.5 μm or more in which microdefects gather in a colony state in a silicon wafer;

selecting the silicon wafer not having the defect; and fabricating the semiconductor device by using the silicon wafer not having the defect.

6. A silicon wafer which is mirror polished and has no defect having the entire defect size of 0.5 μm or more in which microdefects gather in a colony state.

* * * * *